(12) United States Patent
Korte et al.

(10) Patent No.: US 8,476,459 B2
(45) Date of Patent: Jul. 2, 2013

(54) PROCESS FOR THE PREPARATION OF 4-SULFINYL-PYRAZOLE DERIVATIVES

(75) Inventors: Alexander Korte, Sao Paulo (BR); Paul Hornung, Ruessingen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/504,574

(22) PCT Filed: Oct. 26, 2010

(86) PCT No.: PCT/EP2010/066162
§ 371 (c)(1),
(2), (4) Date: Apr. 27, 2012

(87) PCT Pub. No.: WO2011/051284
PCT Pub. Date: May 5, 2011

(65) Prior Publication Data
US 2012/0215008 A1    Aug. 23, 2012

(30) Foreign Application Priority Data

Oct. 30, 2009  (EP) .................................. 09174558

(51) Int. Cl.
*C07D 231/44*  (2006.01)
(52) U.S. Cl.
USPC ....................................................... 548/367.4
(58) Field of Classification Search
None
See application file for complete search history.

(56) References Cited

U.S. PATENT DOCUMENTS 6,881,848 B2 *   4/2005   Clavel et al. ............... 548/366.1

FOREIGN PATENT DOCUMENTS

| CN | 101168529 | 4/2008 |
|---|---|---|
| CN | 101250158 | 8/2008 |
| WO | WO 01/30760 | 5/2001 |
| WO | WO 2007/122440 | 11/2007 |
| WO | WO 2009/077853 | 6/2009 |
| WO | WO 2010/105969 | 9/2010 |

OTHER PUBLICATIONS

International Search Report completed Dec. 9, 2012, in International Application No. PCT/EP2010/066162, filed Oct. 26, 2010.
English language translation of the International Preliminary Report on Patentability dated May 1, 2012, from corresponding International Application No. PCT/EP2010/066162, filed Oct. 26, 2010.
Tang, Ri-Yuan, et al., "A convenient conversion of pyrazolyl disulfide to sulfides by sodium dithionite and synthesis of sulfoxides", Journal of Fluorine Chemistry, 2006, p. 948-953, vol. 127.

* cited by examiner

*Primary Examiner* — Kamal Saeed
(74) *Attorney, Agent, or Firm* — Brinks Hofer Gilson & Lione

(57) ABSTRACT

The present invention relates to a novel process for the preparation of a compound of formula (I),

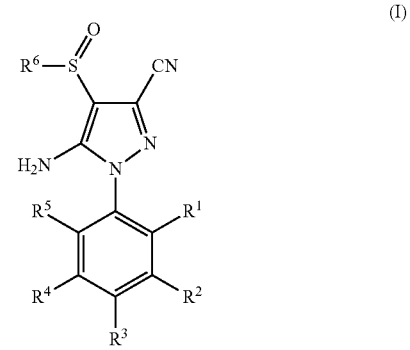

(I)

wherein $R^1$, $R^2$, $R^3$, $R^4$ and $R^5$ are each independently selected from hydrogen, halogen, $C_1$-$C_4$-alkyl, $C_1$-$C_4$-haloalkyl, $C_1$-$C_4$-alkoxy, $C_1$-$C_4$-haloalkoxy, nitro, cyano, and pentafluorothio; $R^6$ is $C_1$-$C_4$-alkyl, or $C_1$-$C_4$-haloalkyl; by oxidation of a compound of formula (II)

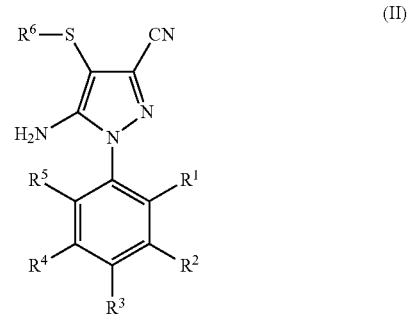

(II)

with an oxidation agent selected from trifluoroperacetic acid and trichloroperacetic acid in the presence of a catalyst selected from hydroxides, oxides, sulfates, acetates or trifluoroacetates of lithium, magnesium, calcium, strontium, barium, titanium (IV), zinc (II) and manganese (II).

19 Claims, No Drawings

PROCESS FOR THE PREPARATION OF 4-SULFINYL-PYRAZOLE DERIVATIVES

This application is a National Stage application of International Application No. PCT/EP2010/066162, filed Oct. 26, 2010, the entire contents of which is hereby incorporated herein by reference. This application also claims priority under 35 U.S.C. §119 to European Patent Application No. 09174558.8, filed Oct. 30, 2009, the entire contents of which is hereby incorporated herein by reference.

The present invention relates to a novel process for the preparation of a compound of formula (I),

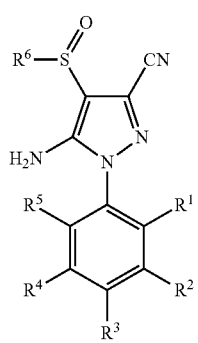

wherein
$R^1$, $R^2$, $R^3$, $R^4$ and $R^5$ are each independently selected from hydrogen, halogen, $C_1$-$C_4$-alkyl, $C_1$-$C_4$-haloalkyl, $C_1$-$C_4$-alkoxy, $C_1$-$C_4$-haloalkoxy, nitro, cyano, and pentafluorothio; and
$R^6$ is $C_1$-$C_4$-alkyl, or $C_1$-$C_4$-haloalkyl;
by oxidation of a compound of formula (II)

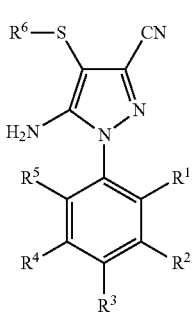

wherein $R^1$, $R^2$, $R^3$, $R^4$, $R^5$, and $R^6$ areas defined for compounds of formula (I), with an oxidation agent selected from trifluoroperacetic acid and trichloroperacetic acid in the presence of a catalyst selected from hydroxides, oxides, sulfates, acetates or trifluoroacetates of lithium, magnesium, calcium, strontium, barium, titanium (IV), zinc (II) and manganese (II).

4-Sulfinyl-pyrazole derivatives of formula (I) are important pesticides. Especially important 4-sulfinyl-pyrazole derivatives are fipronil and ethiprole.

The preparation of certain phenylpyrazoles carrying a sulfinyl- or sulfonyl-group by oxidation of the sulfur atoms from the corresponding alkylthio, alkenylthio- or alkynylthio compounds is generally given in EP-A1 295177. As possible oxidants, hydrogen peroxide, trifluoroperacetic acid formed in situ from trifluoroacetic acid anhydride and hydrogen peroxide, trifluoroperacetic acid anhydride or preferably 3-chloroperbenzoic acid in solvents such as dichloromethane, chloroform, trifluoroacetic acid are mentioned. Alternatively, potassium hydrogen persulphate or potassium salt of Caro's acid in solvents such as methanol or water are given as oxidants.

A number of documents deal with the oxidation of a compound of formula (II) with an aim to prepare a compound of formula (I), especially fipronil.

In IPCOM000156770D, the oxidation of a compound of formula (II) with hydrogenperoxide in dichloromethane as solvent and in the presence of trifluoroacetic acid is described. CN 101250158A mentions the catalytic oxidation of a compound of formula (II) with hydrogenperoxide and sulphuric acid in an inert solvent (monochlorobenzene, chloroform), but fails to specify the structure of the catalyst. Similarly, the catalytic oxidation a compound of formula (II) with hydrogenperoxide in dichloromethane is mentioned in Shanghai Chemical Industry 2007, 7 (32), 17, but no details on the structure of the catalyst are given.

CN 101168529A teaches the oxidation of a compound of formula (II) with trichloroisocyanic acid in a solvent mixture of an ionic liquid and acetonitrile in the presence of ruthenium trichloride as catalyst. Similarly, in Journal of Fluorine Chemistry 2006, 127, 948, the oxidation a compound of formula (II) with trichloroisocyanic acid in dichloromethane as solvent is mentioned.

WO 2007/122440 teaches the oxidation of a compound of formula (II) with trichloroacetic acid/hydrogenperoxide in dichloro acetic acid or dichloromethane.

WO 2009/077853 lists a number of agents for the oxidation of a compound of formula (II): trifluoracetic acid and oxone; trifluoromethane sulfonic acid anhydride and hydrogenperoxide in ethanol; cyclohexylidenebishydroperoxide, sodium iodide and hydrogenperoxide in acetonitrile; cerammoniumbromide, sodium bromate and silica gel in dichloromethane; and hydrogenperoxide plus catalytical amounts of HAuCl4 in methanol.

The above mentioned processes for the oxidation of compounds of formula (II) to yield compounds of formula (I) are not entirely satisfying. Criteria for suitable large-scale oxidation processes are the following: (1) highly selective oxidation to the sulfoxide product of formula (I) (i.e. yielding low amounts of the sulfone by-product wherein the $S(=O)R^6$-group in compounds of formula (I) is overoxidized to a $S(=O)_2R^6$-group); (2) high yield of compounds of formula (I); (3) inhibition of corrosion due to in situ formation of hydrogen fluoride during the oxidation; (4) high reaction rate of the oxidation (determines the productivity). To date, the by far most appropriate combination to solve issues (1), (2) and (3) is discussed by WO01/30760 that describes the oxidation of a compound of formula (II) with trifluoroperacetic acid in the presence of a corrosion inhibiting compound. However, the reaction rate for that process that determines the productivity is still not as high as desirable for a large-scale technical process.

It was therefore an object of the present invention to provide a new and improved oxidation process of compounds (II) to compound (I). Specifically, it was an object to provide a new and improved oxidation process of compounds (II) to compounds (I) with an improved (higher) reaction rate. In a preferred embodiment, it was an object to provide a new and improved catalytic oxidation process of compounds (II) to compounds (I) wherein the catalyst can be easily removed (e.g. by washing with water) from the reaction product.

Accordingly, the inventive process defined at the outset was found. Surprisingly, the addition of compounds selected from hydroxides, oxides, sulfates, acetates, or trifluoroacetates of lithium, magnesium, calcium, strontium, barium, titanium, zinc and manganese increased the reaction rate significantly, thereby increasing the productivity (produced product per time)

The present invention can be used to prepare fipronil as an intermediate compound for the preparation of butene fipronil (compound III). Butene fipronil is obtained by alkylation of fipronil, as described in CN 3198515.

(III)

The substituents have the following meanings:

The term halogen denotes in each case fluorine, bromine, chlorine or iodine, in particular fluorine, chlorine or bromine, preferably chlorine or fluorine.

The term "$C_1$-$C_4$-alkyl" as used herein refers to a saturated straight-chain or branched hydrocarbon group having 1 to 4 carbon atoms, for example methyl, ethyl, propyl, 1-methylethyl, butyl, 1-methylpropyl, 2-methylpropyl, and 1,1-dimethylethyl.

The term "$C_1$-$C_4$-haloalkyl" as used herein refers to a straight-chain or branched saturated alkyl group having 1 to 4 carbon atoms (as mentioned above), where some or all of the hydrogen atoms in these groups may be replaced by halogen atoms as mentioned above, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_4$-alkoxy" as used herein refers to a straight-chain or branched saturated alkyl group having 1 to 4 carbon atoms (as mentioned above) which is attached via an oxygen atom. Examples include methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, and $OC(CH_3)_3$.

The term "$C_1$-$C_4$-haloalkoxy" as used herein refers to a $C_1$-$C_4$-alkoxy group as mentioned above wherein the hydrogen atoms are partially or fully substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, in particular chloromethoxy, fluoromethoxy, difluoromethoxy, trifluoromethoxy, 2-fluoroethoxy, 2-chloroethoxy or 2,2,2-trifluoroethoxy.

With regard to the inventive process, the substituents of compounds of formulae (I) and (II) preferably have the following meanings:

$R^1$ and $R^5$ are preferably selected from halogen and $C_1$-$C_4$-haloalkyl, even more preferably from chlorine, fluorine and trifluoromethyl, most preferably from chlorine.

$R^2$ and $R^4$ preferably are hydrogen.

$R^3$ preferably is $C_1$-$C_4$-alkyl, $C_1$-$C_4$-haloalkyl or pentafluorothio, even more preferably $C_1$-$C_4$-haloalkyl, and most preferably trifluoromethyl.

$R^6$ preferably is ethyl or trifluoromethyl.

$R^6$ preferably is ethyl.

$R^6$ most preferably is trifluoromethyl.

Most preferably, the substituents of compounds of formulae (I) and (II) have the following meanings:

$R^1$ and $R^5$ are chlorine;

$R^2$ and $R^4$ are hydrogen;

$R^3$ is trifluoromethyl; and $R^6$ is ethyl or trifluoromethyl, preferably trifluoromethyl.

In an especially preferred embodiment, the inventive process is employed to prepare the compounds I-1 or I-2 of Scheme I.

Scheme I (I-1: fipronil)         (I-2: ethiprole)

Most preferably, the inventive process is employed to prepare fipronil.

Compounds of formula (II) can be obtained according to procedures described in the literature, such as in WO 01/30760, WO 05/44806, and EP-A1 295 117.

Suitable oxidating agents are trifluoroperacetic acid (e.g. formed in situ from trifluoroacetic acid and hydrogen peroxide) or trichloroperacetic acid (e.g. formed in situ from trichloroacetic acid and hydrogen peroxide). Preferred is trifluoroperacetic acid. Most preferably, trifluoroperacetic acid formed in situ from trifluoroacetic acid and hydrogen peroxide is used. The hydrogen peroxide generally is used as a 50% w/w aqueous solution and is generally from about 1.0 to about 2.0 equivalents, preferably about 1.2 to 1.6 equivalents, more preferably about 1.30 to 1.45 equivalents and even more preferably about 1.35 to 1.40 equivalents relative to compounds of formula (II).

The inventive process is preferably conducted in a solvent selected from trifluoroacetic acid, mixtures of trifluoroacetic acid and monochlorobenzene or trifluoroacetic acid and dichloromethane, and mixtures of trichloroacetic acid with a melting point depressant such as monochlorobenzene, monochloroacetic acid, dichloroacetic acid, dichloroethane, and dichloromethane.

If a mixture of trichloroacetic acid and a melting point depressant is used, the melting point depressant generally is used in 20% to 30% w/w of the trichloroacetic acid. Preferably, 1.0 to 2.0 liter of trichloroacetic acid is used per mol of compound of formula (II).

Preferred solvent is trifluoroacetic acid. Preferably, about 10 to about 20 mol of trifluoroacetic acid relative to employed molar amounts of compound (II) is used, more preferably about 14 to 16 molar equivalents, and most preferably about 15.2 to 15.8 molar equivalents.

In a preferred aspect of the present invention, trifluoroacetic acid is used as the solvent and mono chlorobenzene is added to reaction mixture upon completion of the reaction, followed by removal of trifluoroacetic acid by azeotropic distillation.

The catalyst is selected from the hydroxides, oxides, sulfates, acetates, or trifluoroacetates of lithium, magnesium, calcium, strontium, barium, titanium (IV), zinc (II) and manganese (II).

Examples are: LiOH (lithium hydroxide), $Mg(OH)_2$ (magnesium hydroxide), $Ca(OH)_2$ (calcium hydroxide), $Sr(OH)_2$ (strontium hydroxide), $Ba(OH)_2$ (barium hydroxide), $Mn(OH)_2$ (manganese (II) hydroxide), MgOH (magnesium oxide), CaO (calcium oxide), BaO (barium oxide), $TiO_2$ (titanium dioxide), ZnO (zinc (II) oxide), MnO (manganese (II) oxide), magnesium trifluoroacetate, calcium trifluoroacetate, barium trifluoroacetate, strontium trifluoroacetate, zinc trifluoroacetate, manganese trifluoroacetate, magnesium acetate, calcium acetate, barium acetate, strontium acetate, zinc acetate, manganese acetate, magnesium sulfate, calcium sulfate, barium sulfate, strontium sulfate, zinc sulfate, manganese sulfate.

Preferred are catalysts of the list give above which are commercially available.

The metal cation is preferably selected from cations of lithium, magnesium, calcium, strontium, barium, titanium (IV), zinc (II), and manganese (II), most preferably from calcium, barium, strontium and zinc (II). Especially preferred cation is zinc (II).

Preferred catalysts are selected from the group of hydroxides of lithium, magnesium, calcium, strontium, and barium, and oxides of calcium, barium, titanium (IV), zinc (II), and manganese (II).

Preferred are hydroxides of lithium, magnesium, calcium, strontium, and barium, especially of calcium, strontium, and barium.

Preferred are oxides of calcium, barium, titanium (IV), zinc (II), and manganese (II). Most preferred catalysts are ZnO and CaO. Especially preferred is ZnO. Also, especially preferred is CaO.

Preferred are trifluoroacetates of calcium and zinc (II), especially of calcium.

Also preferred are acetates of calcium and zinc (II), especially of calcium.

Preferred are sulfates of magnesium, calcium, strontium, barium, and zinc (II), especially of calcium, strontium, and barium.

The inventive process can be conducted in the presence of a fluoride corrosion inhibitor selected from boric acid, alkali metal borates, and silica, preferably boric acid. In case trifluoroacetic acid is used as a solvent, it is advantageous to conduct the process in the presence of a fluoride corrosion inhibitor. The amount of corrosion inhibiting compound used is generally about 0.01 to 0.99 molar equivalents relative to compound of formula (II), preferably about 0.01 to 0.2 molar equivalents, more preferably about 0.03 to 0.15 molar equivalents, and most preferably about 0.06 to 0.1 molar equivalents.

The inventive process is preferably conducted at temperatures of −40° C. to 80° C., more preferably of 0° C. to 60° C., even more preferably of 10° C. to 30° C., and even more preferably between 10° C. to 20° C. Most preferably, the inventive process is conducted at 10° C. to 15° C., advantageously at 12° C.

The reaction rate depends upon the temperature, and the favorable effect of increasing the reaction rate can be observed over the whole temperature range. When conducted according to the inventive process, i.e. in the presence of the catalyst, the reaction rate is higher than the rate of a reaction carried out at the same temperature but without addition of catalyst.

If the oxidation reaction is judged to be complete, the reaction is preferably quenched sulfur dioxide, sodium sulfite, or equivalent reagents. In the case trifluoroacetic acid was used as a solvent, it is preferably removed by addition of monochlorbenzene followed by azeoptropic distillation under reduced pressure. In a preferred embodiment, an alcohols such as ethanol, methanol or isopropanol is added to the residue, and warmed to about 80° C. until a solution is formed, and then cooled to about 40° C. when the compound of formula (I) crystallizes.

The isolated compounds of formula (I) can be purified by a technique such as chromatography, recrystallization and the like, if necessary. Purification of the crude product can also be achieved via filtration over charcoal or silica or washing with water.

The crystallization of the compounds of formula (I) such as ethiprole or fipronil, preferably fipronil, is typically conducted from a solution in a nonpolar, inert, preferably aromatic solvent with nonreactive substituents such as chloro, fluoro, cyano, nitro, $C_1$-$C_8$-alkyl, or $C_1$-$C_8$-haloalkyl, particularly from a solution in benzene, ethylbenzene, monochlorobenzene, monofluorobenzene, 1,2-dichlorobenzene, 1,3-dichlorobenzene, 1,4-dichlorobenzene, toluene, o-xylene, m-xylene, p-xylene, styrene, i-propyl benzene, n-propyl benzene, 2-chlorotoluene, 3-chlorotoluene, 4-chlorotoluene, tert.-butyl benzene, sec.-butyl benzene, iso-butyl benzene, n-butyl benzene, 1,3-diisopropylbenzene, 1,4-diisopropylbenzene, 2-nitrotoluene, 3-nitrotoluene, 4-nitrotoluene, nitrobenzene, benzonitrile, mesitylene, trifluoromethyl benzene, 1,2-dichloroethane, acetonitrile, dimethylsulfoxide, tetrahydrofuran, acetone, alcohols such as methanol, ethanol, n-propanol, isopropanol, n-butanol, isobutanol, 2-butanol, or tert-butanol, or mixtures thereof, preferably from a solution in monochlorobenzene, dichlorobenzene, ethylbenzene or toluene.

Preferably, the crystallization is done from monochlorobenzene.

Preferably, the crystallization is done from dichlorobenzene.

Preferably, the crystallization is done from ethylbenzene.

Preferably, the crystallization is done from toluene.

It can be advantageous to add about 1 to 30 percent of a polar solvent such as ketons, amides, alcohols, esters or ethers, preferably esters, ketons or ethers, such as acetone methyl ethyl ketone, pentan-2-one, diethylketone, 4-methyl-2-pentanone, 3-methyl-butan-2-one, tert-butyl-methyl-ketone, cyclohexanone, methylacetate, ethylacetate, isopropylacetate, N-butylacetate, isobutylacetate, diethylcarbonate, 2-butoxyethylacetate, dimethylformamide, dimethylacetamide, dimethylsulfoxide, nitromethane, nitroethane, water, ethanol, methanol, propan-1-ol, propan-2-ol, butan-1-ol, butan-2-ol, tert-butanol, 2-methyl-propan-1-ol, 2-methyl-propan-2-ol, pentan-3-ol, 2-methyl butan-1-ol, 3-methyl butan-1-ol, 1,2-ethanediol, 1,3-propandiol, 1,2-propandiol, cyclohexanol, dioxane, tetrahydrofurane, diethylether, methyl tert.-butyl ether, 2-methyl tetrahydrofuran, acetonitrile, propionitrile, or mixtures thereof.

EXAMPLES

Reactions were conducted according to the procedures given below in example 1, 2 and in the comparative example. The reaction rate was measured by HPLC in all cases to monitor the conversion of the starting material to the desired sulfoxide. The end of the reaction was determined once a sulfide amount >97% and a sulfone amount of >2% was detected by HPLC.

HPLCs were taken on a Hewlett Packard HP 1050, Chemstation, equipped with a Chromolith RP18e, 100×3 mm column (Merck), eluent: 450 mL water+330 mL acetonitrile+220 mL MeOH+1 mL phosphoric acid, flow: 1.0 ml/min, detection: 220 nm.

Each experiment was done twice. The procedures described in Examples 1 and 2 were used to conduct further preparation experiments with different catalysts and/or different molar equivalents of catalysts by respective modification. The results of the experiments are listed in Table I which follows.

Example 1

Preparation of Fipronil in the Presence of ZnO as a Catalyst

Fipronil was obtained by oxidation of 5-amino-3-cyano-1-(2,6-dichloro-4-trifluoromethylphenyl)-4-trifluoromethylthiopyrazole (105.3 g, 0.25 mol) with a 50% w/w aqueous solution of hydrogen peroxide (23.6 g, 0.35 mol) in trifluoroacetic acid (443.4 g, 3.89 mol) in presence of ZnO (4.9 g, 0.06 mol) at 10-12° C. After completion of reaction after 4 hours (conversion >97% according to HPLC analysis), the reaction was quenched with $SO_2$ before monochlorobenzene was added and trifluoroacetic acid was removed by azeotropic distillation under reduced pressure. The residue was crystallized from monochlorobenzene/ethanol. Ethanol was removed by distillation under reduced pressure and the suspension was filtered at 10° C. Washing with monochlorobenzene, ethanol/water and water followed by drying under vacuum afforded fipronil as a colorless solid (96 to 97 g, purity >95 weight % according to HPLC).

Example 2

Preparation of Fipronil in the Presence of ZnO as a Catalyst and with Addition of a Corrosion Inhibitor Fipronil was obtained by oxidation of 5-amino-3-cyano-1-(2,6-dichloro-4-trifluoromethylphenyl)-4-trifluoromethylthiopyrazole (105.3 g, 0.25 mol) with a 50% w/w aqueous solution of hydrogen peroxide (23.6 g, 0.35 mol) in trifluoroacetic acid (443.4 g, 3.89 mol) in presence of boric acid (1.3 g, 0.02 mol) and ZnO (4.9 g, 0.06 mol) at 10-12° C. After completion of reaction in 4 hours (conversion >97% according to HPLC analysis) the reaction was quenched with $SO_2$ before monochlorobenzene was added and trifluoroacetic acid was removed by azeotropic distillation under reduced pressure. The residue was crystallized from monochlorobenzene/ethanol. Ethanol was removed by distillation under reduced pressure and the suspension was filtered at 10° C. Washing with monochlorobenzene, ethanol/water and water followed by drying under vacuum afforded fipronil as a colorless solid (94 to 96 g, purity >95 weight % according to HPLC).

Comparative Example

Preparation of Fipronil without the Addition of a Catalyst

The reaction was conducted as described above for example 2, but without the addition of a catalyst. The reaction was completed within 6.5 hours (conversion more than 97% according to HPLC analysis). Fipronil was obtained as a colorless solid (96-97 g, purity >95 weight % according to HPLC).

TABLE 1

Preparation of Fipronil

| Example No | Catalyst | mol | $B(OH)_3$ addition [mol] | Temperature [° C.] | Completion of reaction after [hours][#] |
|---|---|---|---|---|---|
| 1 | ZnO | 0.06 | — | 10-12° C. | 4 |
| 2 | ZnO | 0.06 | 0.02 | 10-12° C. | 4 |
| 3 | ZnO | 0.12 | — | 10-12° C. | 3.5 |
| 4 | ZnO | 0.03 | — | 10-12° C. | 4.5 |
| 5 | ZnO | 0.06 | — | 5-7° C. | 6 |
| 6 | ZnO | 0.06 | — | 15-17° C. | 3.5 |
| 7 | CaO | 0.06 | — | 10-12° C. | 3-4 |
| 8 | CaO | 0.06 | 0.02 | 10-12° C. | 3-4 |
| 9 | CaO | 0.12 | — | 10-12° C. | 3 |
| 10 | CaO | 0.03 | — | 10-12° C. | 4 |
| 11 | CaO | 0.06 | — | 5-7° C. | 5 |
| 12 | CaO | 0.06 | — | 15-17° C. | 3 |
| 13 | BaO | 0.06 | — | 10-12° C. | 4.5 |
| 14 | MnO | 0.06 | — | 10-12° C. | 6 |
| 15 | $TiO_2$ | 0.06 | — | 10-12° C. | 6.25 |
| 16 | $Ca(OH)_2$ | 0.06 | — | 10-12° C. | 4 |
| 17 | $Ca(OH)_2$ | 0.03 | — | 10-12° C. | 5 |
| 18 | $Mg(OH)_2$ | 0.06 | — | 10-12° C. | 6 |
| 19 | LiOH | 0.12 | — | 10-12° C. | 6 |
| 20 | $Ba(OH)_2$ | 0.06 | — | 10-12° C. | 4.5 |
| 21 | $Sr(OH)_2$ | 0.06 | — | 10-12° C. | 4 |
| 22 | $CaSO_4$ | 0.06 | — | 10-12° C. | 6 |
| 23 | calcium acetate | 0.06 | — | 10-12° C. | 3.5 |
| Comparative Example | none | — | 0.02 | 10-12° C. | 6.5 |

[#]conversion more than 97% according to HPLC analysis

The invention claimed is:
1. A process for preparing a compound of formula (I),

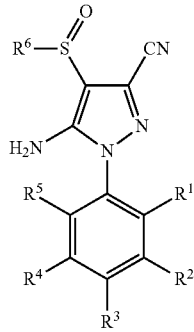

wherein
$R^1, R^2, R^3, R^4$ and $R^5$ are each independently selected from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy, nitro, cyano, and pentafluorothio; and
$R^6$ is $C_1$-$C_4$-alkyl or $C_1$-$C_4$-haloalkyl;
comprising oxidizing a compound of formula (II)

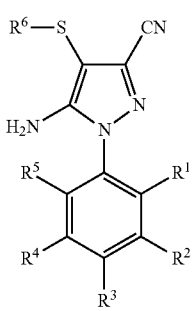

with an oxidation agent selected from the group consisting of trifluoroperacetic acid and trichloroperacetic acid in the presence of a catalyst selected from the group consisting of hydroxides, oxides, sulfates, acetates or trifluoroacetates of lithium, magnesium, calcium, strontium, barium, titanium (IV), zinc (II) and manganese (II).

2. The process according to claim 1, wherein
$R^1$ and $R^5$ are chlorine;
$R^2$ and $R^4$ are hydrogen; and
$R^3$ is trifluoromethyl.

3. The process according to claim 1, wherein
$R^6$ is trifluoromethyl or ethyl.

4. The process according to claim 1, wherein the oxidation reaction is conducted in a solvent selected from the group consisting of trifluoroacetic acid, a mixture of trifluoroacetic acid and monochlorobenzene, a mixture of trifluoroacetic acid and dichloromethane, and a mixture of trichloroacetic acid and a melting point depressant.

5. The process according to claim 4, wherein the melting point depressant is selected from the group consisting of monochlorobenzene, monochloroacetic acid, dichloroacetic acid, dichloroethane, and dichloromethane.

6. The process according to claim 5, wherein
$R^1$ and $R^5$ are chlorine;
$R^2$ and $R^4$ are hydrogen; and
$R^3$ is trifluoromethyl.

7. The process according to claim 6, wherein
$R^6$ is trifluoromethyl or ethyl.

8. The process according to claim 1, wherein the oxidation reaction is conducted in trifluoroacetic acid as a solvent.

9. The process according to claim 1, wherein the metal cation is selected from the group consisting of cations of lithium, magnesium, calcium, strontium, barium, titanium (IV), zinc (II), and manganese (II).

10. The process according to claim 1, wherein the catalyst is selected from the group consisting of hydroxides of lithium, magnesium, calcium, strontium, and barium, and oxides of calcium, barium, titanium (IV), zinc (II), and manganese (II).

11. The process according to claim 10, wherein
$R^1$ and $R^5$ are chlorine;
$R^2$ and $R^4$ are hydrogen; and
$R^3$ is trifluoromethyl.

12. The process according to claim 11, wherein
$R^6$ is trifluoromethyl or ethyl.

13. The process according to claim 12, wherein the oxidation reaction is conducted at temperatures of 0° C. to 40° C.

14. The process according to claim 1, wherein the catalyst is ZnO or CaO.

15. The process according to claim 1 wherein the oxidation reaction is conducted in the presence of a fluoride corrosion inhibitor selected from the group consisting of boric acid, alkali metal borates, and silica.

16. The process according to claim 1, wherein the oxidation reaction is conducted at temperatures of 0° C. to 40° C.

17. The process according to claim 15, wherein
$R^1$ and $R^5$ are chlorine;
$R^2$ and $R^4$ are hydrogen; and
$R^3$ is trifluoromethyl.

18. The process according to claim 17, wherein
$R^6$ is trifluoromethyl or ethyl.

19. The process according to claim 18, wherein the oxidation reaction is conducted at temperatures of 0° C. to 40° C.

* * * * *